(12) United States Patent
Wei

(10) Patent No.: US 11,612,475 B2
(45) Date of Patent: Mar. 28, 2023

(54) BLOOD CONDUIT WITH STENT

(71) Applicants: Jeng Wei, Taipei (TW); Tai-Yen Sun, South Euclid, OH (US)

(72) Inventor: Jeng Wei, Taipei (TW)

(73) Assignees: Jeng Wei, Taipei (TW); Tai-Yen Sun, South Euclid, OH (US)

( * ) Notice: Subject to any disclaimer, the term of this patent is extended or adjusted under 35 U.S.C. 154(b) by 155 days.

(21) Appl. No.: 16/340,645

(22) PCT Filed: Oct. 10, 2017

(86) PCT No.: PCT/IB2017/056247
§ 371 (c)(1),
(2) Date: Apr. 9, 2019

(87) PCT Pub. No.: WO2018/069828
PCT Pub. Date: Apr. 19, 2018

(65) Prior Publication Data
US 2020/0046487 A1 Feb. 13, 2020

Related U.S. Application Data

(60) Provisional application No. 62/405,997, filed on Oct. 10, 2016.

(51) Int. Cl.
*A61F 2/07* (2013.01)

(52) U.S. Cl.
CPC .......... *A61F 2/07* (2013.01); *A61F 2002/077* (2013.01); *A61F 2210/0014* (2013.01);
(Continued)

(58) Field of Classification Search
CPC ................ A61F 2/07; A61F 2250/0048; A61F 2250/0018; A61F 2/06; A61F 2250/0029; A61B 2017/00243; Y10S 623/903
(Continued)

(56) References Cited

U.S. PATENT DOCUMENTS 5,360,443 A * 11/1994 Barone ...................... A61F 2/07
623/1.13
6,027,526 A 2/2000 Limon et al.
(Continued)

FOREIGN PATENT DOCUMENTS

EP      1336393 A2   8/2003
EP      1137374 B1   4/2009

OTHER PUBLICATIONS

Canadian Intellectual Property Office, Requisition by the Examiner (Office Action) for CA application No. 3,048,464, dated Oct. 9, 2020.
(Continued)

*Primary Examiner* — Brian E Pellegrino
(74) *Attorney, Agent, or Firm* — Birch, Stewart, Kolasch & Birch, LLP

(57) ABSTRACT

A blood conduit with stent has a flexible conduit body and an expandable stent structure. The conduit body has a first opening end through which only an inflow of a blood enters and a second opening end through which only an outflow of the blood leaves. The stent structure includes a plurality of threads adhered to the conduit body and expands in directions intersecting an axial direction of the conduit body. A boundary of one of the threads of the stent structure closest to the second opening end is away from the second opening end with a predetermined distance, thereby preventing blood back flow into the false lumen via a new tear.

7 Claims, 11 Drawing Sheets

(52) U.S. Cl.
CPC .............. *A61F 2230/0056* (2013.01); *A61F 2250/0018* (2013.01); *A61F 2250/0048* (2013.01)

(58) Field of Classification Search
USPC ........................................................ 623/1.32
See application file for complete search history.

(56) References Cited

U.S. PATENT DOCUMENTS

| | | | |
|---|---|---|---|
| 6,585,758 B1 * | 7/2003 | Chouinard | A61F 2/90 623/1.16 |
| 6,773,457 B2 * | 8/2004 | Ivancev | A61F 2/07 623/1.13 |
| 8,317,854 B1 | 11/2012 | Ryan et al. | |
| 2002/0198588 A1 | 12/2002 | Armstrong et al. | |
| 2003/0074049 A1 | 4/2003 | Hoganson et al. | |
| 2003/0176912 A1 | 9/2003 | Chuter et al. | |
| 2005/0177222 A1 * | 8/2005 | Mead | A61F 2/07 623/1.13 |
| 2007/0179590 A1 * | 8/2007 | Lu | A61F 2/91 623/1.16 |
| 2008/0132993 A1 * | 6/2008 | Rasmussen | A61F 2/07 623/1.13 |
| 2013/0197627 A1 | 8/2013 | Jensen et al. | |
| 2015/0034217 A1 | 2/2015 | Vad | |
| 2015/0164665 A1 | 6/2015 | Cam et al. | |
| 2015/0320578 A1 | 11/2015 | Bui et al. | |

OTHER PUBLICATIONS

European Patent Office, extended European search report for EP application No. 17860771.9, dated Sep. 9, 2020.

* cited by examiner

BLOOD CONDUIT WITH STENT

TECHNICAL FIELD

The present disclosure relates to a blood conduit and, more in particular to, a blood conduit with stent.

BACKGROUND

The largest blood vessel extending from the human heart is the aorta. The aorta is divided into the thoracic aorta (aorta thoracalis) and the abdominal aorta (aorta abdominalis), among which the thoracic aorta is further divided into the ascending aorta (aorta ascendens), the aortic arch (arcus aortae), and the descending aorta (aorta descendens), and the abdominal aorta is further divided into the suprarenal abdominal aorta (aorta abdominalis suprarenalis) and the infrarenal abdominal aorta (aorta abdominalis infrarenalis). The cross section of the aortic wall is divided into three layers from the inside out: the tunica intima, which is the innermost layer that defines the border of the aortic true lumen, the tunica media, which is the middle layer, and the tunica adventitia, which is the outermost layer. Common aortic diseases include aortic aneurysm and aortic dissection. Aortic dissection occurs when the innermost layer of the aorta, tunica intima, tears, thereby allowing blood to flow through the tear and enter between the tunica intima and the tunica media. The force exerted by the blood flowing between the tunica intima and the tunica media leads to tears and separation between the tunica intima and the tunica media, and results in the formation of a false lumen between the tunica intima and the tunica media. The false lumen can compress the space of the true lumen and cause insufficient blood supply for various body parts, leading to ischemia of the limbs or the brain. Additionally, because the lining of the false lumen is not an intact vascular wall structure and is more fragile, the continuous blood flowing into the false lumen through the tear often leads to rupture of the false lumen and therefore hemorrhage, posing a significant life-threatening risk to an individual.

Since 1990, the industry has developed a technique of implanting endovascular stent-graft into the vascular lumen of the aorta for treating aortic diseases. (Please refer to the internet textbook, Textbook of Cardiovascular Intervention, Chapter 34, by Craig A. Thompson, published in 2014). Please refer to FIG. 1. An endovascular stent-graft 10 comprises a metallic stent 20 covering an artificial blood vessel 30, and may be placed in the thoracic aorta or the abdominal aorta and fixed at the aortic lesion location requiring implantation of the endovascular stent-graft 10 by the anchoring force and by the thrust against the aorta, wherein the anchoring force is generated by anchoring a proximal end 45 at the aorta and the thrust against the aorta comes from spontaneous expansion of the metallic stent 20 along the radial direction of artificial blood vessel 30. Please simultaneously refer to both FIG. 1 and FIG. 2. The use of the endovascular stent-graft 10 is to separate a tear 60 in the tunica intima of an aorta 50 from the blood flow, allowing the blood to flow within the artificial blood vessel 30 of the endovascular stent-graft 10 without entering a false lumen 70 through the tear 60 and leading to continuous dilation or rupture of the false lumen 70. Additionally, with reducing blood in the false lumen 70, the false lumen 70 will not further compress the space of the true lumen, thereby allowing the space of the true lumen to gradually revert to the original state, and further allowing a relatively sufficient blood supply to various tissues in the body.

However, since the development of the technique of implanting the endovascular stent-graft 10 into the vascular lumen of the aorta in 1990, the industry continues to discover that implantation of the endovascular stent-graft 10 may cause further injuries to the tunica intima near the distal end 40 of the endovascular stent-graft 10, resulting in the formation of a new tear (Stent-graft Induced New Entry, SINE) 80 and therefore cause the formation of a new false lumen, or therefore cause the blood near the distal end 40 of the endovascular stent-graft 10 to back flow into the original false lumen which result in the dilation of the original false lumen. In other words, although implantation of the endovascular stent-graft 10 solve the problem at the original tear 60, it leads to the formation of the new tear 80 at the distal end 40, and reintroduces the issue of true lumen compression by the false lumen and the risk of false lumen rupture. As demonstrated by a reference published in 2013, the incidence of new tear formation caused by implantation of the endovascular stent-graft 10 is as high as 60%. (Please refer to the abstract of the article published by Huang et al. in 2013.) Especially, when the volume of the implanted endovascular stent-graft 10 is larger, it is more likely that this issue may occur. In order to solve this issue, people have tried to decrease the caliber of the distal end 40 of the endovascular stent-graft 10, but because the aortic vascular wall is no longer an intact vascular wall structure and is fragile, it is easily to form the new tear 80 under the influence of the metallic stent 20 at the distal end 40. Currently, while dealing with the formation of new tears in most of the patients, the industry can only implant another endovascular stent-graft at the distal end of the original implanted endovascular stent-graft 10. (Please refer to the abstract of the article published by Jang et al. in 2017, and the abstract of the article published by Wang et al. in 2015.) This further forces the patients to repeatedly face the issue of true lumen compression by the false lumen and the risk of false lumen rupture caused by the new implanted endovascular stent-graft, and tremendously impacts on the life and safety of the patients. To a person having ordinary skill in the art, this issue has existed for 27 years since 1990 without effective solutions, and a technical solution to this long-term issue is much needed.

Non-patent references 1

Factors predictive of distal stent graft-induced new entry after hybrid arch elephant trunk repair with stainless steel-based device in aortic dissection. Huang C Y, Weng S H, Weng C F, Chen W Y, Chen I M, Hsu C P, and Shih C C., 2013. J Thorac Cardiovasc Surg. 146(3):623-630.

Non-patent references 2

Risk factors for stent graft-induced new entry after thoracic endovascular aortic repair for Stanford type B aortic dissection. Hyunsik Jang, Man-Deuk Kim, Gyoung Min Kim, Jong Yun Won, Young-Guk Ko, Donghoon Choi, Hyun-Chul Joo, and Do Yun Lee, 2017. J Vasc Surg. 65(3):676-685.

Non-patent references 3

Risk factors for distal stent graft-induced new entry following endovascular repair of type B aortic dissection. Qing Li, Long-Fei Wang, Wei-Guo Ma, Shang-Dong Xu, Jun Zheng, Xiao-Yan Xing, Lian-Jun Huang, and Li-Zhong Sun, 2015. J Thorac Dis. 7(11):1907-1916.

SUMMARY

In view of the above-mentioned issues, the present disclosure provides a blood conduit with stent having a flexible conduit body and an expandable stent structure. The conduit body has a first opening end through which only an inflow of a blood enters and a second opening end through which only an outflow of the blood leaves. The stent structure includes a plurality of threads adhered to the conduit body and expands in directions intersecting with an axial direction of the conduit body. One of the threads of the stent structure closest to the second opening end is away from the second opening end with a distance being at least 2 cm. As a result, the disclosed blood conduit with stent avoids the blood inside the endovascular wall from flowing back into a false lumen and effectively solves the problem that the blood leaks into the false lumen outside the tunica intima of the aorta.

In one embodiment, the distance between the one of the threads closest to the second opening end and the second opening end may range from 2 cm to 30 cm.

In one embodiment, the threads are adhered to an outer surface of the conduit body. In another embodiment, the threads are adhered to an inner surface of the conduit body.

In one embodiment, an outer surface of a portion of the conduit body within the distance is formed with folds.

In one embodiment, the conduit body may be made of a material selected from polytetrafluoroethylene (PTFE), polyethylene terephthalate (PET), and Dacron. The threads may be made of a material selected from at least one or a combination of nickel-titanium alloys, shape memory alloys excluding the nickel-titanium alloys, and other biomedical metals.

In one embodiment, each of the threads is shaped to have a periodic fluctuated waveform and extend in a direction perpendicular to the axial direction of the conduit, and the boundary of the one of the threads of the stent structure closest to the second opening end neighboring a boundary of the second opening end is a line connecting ridge peaks of the waveform of the closest thread with the ridge peaks neighboring the second opening end.

In one embodiment, a first portion of the conduit body to which the stent structure is adhered is made of a distinct material from that of a second portion of the conduit body within the distance.

The present invention further discloses in still one embodiment a blood conduit with stent including a flexible conduit body and a plurality of expandable threads. The conduit body has a first opening end through which only an inflow of a blood enters and a second opening end through which only an outflow of the blood leaves. The threads are adhered to the conduit body and expandable in directions intersecting with an axial direction of the conduit body. A boundary of a first thread of the threads closest to the first opening end neighboring the first opening end is level with a boundary of the first opening end and a boundary of a second thread of the threads closest to the second opening end neighboring the second opening end is away from a boundary of the second opening end with a distance which is greater than or equal to 2 cm. As a result, the disclosed blood conduit with stent avoids the blood inside the endo-vascular wall from flowing back into a false lumen and effectively solves the problem that the blood leaks into the false lumen outside the tunica intima of the aorta. In another embodiment, the boundary of the first thread of the threads closest to the first opening end neighboring the first opening end is next to the boundary of the first opening end.

In the embodiments, an outer diameter of the conduit body may range from 6 mm to 45 mm, the wall thickness of the conduit body may range from 0.5 mm to 1 mm, and the distance between the boundary of the second thread of the threads closest to the second opening end neighboring the second opening end and the boundary of the second opening end may range from 2 cm to 30 cm.

In one embodiment, the threads are adhered to an outer surface of the conduit body. In another embodiment, the threads are adhered to an inner surface of the conduit body.

In one embodiment, an outer surface of a portion of the conduit body between the second thread and the second opening end is formed with folds In one embodiment, the conduit body may be made of a material selected from polytetrafluoroethylene (PTFE), polyethylene terephthalate (PET), and Dacron. The threads may be made of a material selected from at least one or a combination of nickel-titanium alloys, shape memory alloys excluding the nickel-titanium alloys, and other biomedical metals.

In one embodiment, each of the threads may be shaped to have a periodic or a non-periodic fluctuated waveform. The periodic fluctuated waveform may be one selected from sinusoidal, rectangular, triangular, and jagged waveforms. Each of the threads may extend in a direction perpendicular to an axial direction of the conduit body. The boundary of the first thread neighboring the first opening end is a line connecting ridge peaks of the waveform of the first thread with the ridge peaks neighboring the first opening end, and the boundary of the second thread neighboring the second opening end is a line connecting ridge peaks of the waveform of the second thread with the ridge peaks neighboring the second opening end.

In one embodiment, a first portion of the conduit body between the first thread and the second thread is made of a distinct material from that of a second portion of the conduit body between the second thread and the second opening end.

The present invention still further discloses in one embodiment a blood conduit with stent having a flexible conduit body, a first thread, a second thread, and a third thread. The flexible conduit body has a first opening end through which only an inflow of a blood enters and a second opening end through which only an outflow of the blood leaves. The first thread is disposed to be closest to a boundary of the first opening end, the second thread is disposed to be near a boundary of the second opening end, a boundary of the second thread neighboring the second opening end is away from the boundary of the second opening end with a distance, and the third thread is disposed within the distance. The third thread has a less expansion strength than the second thread, and the distance is greater than or equal to 2 cm. As a result, the disclosed blood conduit with stent avoids the blood inside the endovascular wall from flowing back into a false lumen and effectively solves the problem that the blood leaks into the false lumen outside the tunica intima of the aorta.

In one embodiment, the expansion strength of the third thread is less than or equal to half of the expansion strength of the second thread.

In one embodiment, the first thread, the second thread, and the third thread are adhered to an outer surface of the conduit body. In another embodiment, the first thread, the second thread, and the third thread are adhered to an inner surface of the conduit body. In still one embodiment, only the third thread is adhered to an inner surface of the conduit body while the first thread and the second thread are adhered to an outer surface of the conduit body.

In one embodiment, the conduit body may be made of a material selected from polytetrafluoroethylene (PTFE), polyethylene terephthalate (PET), and Dacron. The threads may be made of a material selected from at least one or a combination of nickel-titanium alloys, shape memory alloys excluding the nickel-titanium alloys, and other biomedical metals.

In one embodiment, each of the first, second and third thread may be shaped to have a periodic or a non-periodic fluctuated waveform. The periodic fluctuated waveform may be one selected from sinusoidal, rectangular, triangular, and jagged waveforms. Each of the first, second and third thread may extend in a direction perpendicular to an axial direction of the conduit body. The boundary of the second thread neighboring the second opening end is a line connecting ridge peaks of the waveform of the second thread with the ridge peaks neighboring the second opening end.

In one embodiment, a first portion of the conduit body between the first thread and the second thread is made of a distinct material from that of a second portion of the conduit body between the second thread and the second opening end.

In the embodiments as mentioned, the effect of applying radial thrust on the aorta via the outward expansion of the stent structure or the threads with larger expansion strength makes the conduit body possessing the stent structure or possessing the threads tightly adhere to the endovascular wall of a human's aorta and cover a tear in the lesion location. The expanded stent structure presses against the endovascular wall of the aorta due to the larger size of the expanded stent structure than the inner diameter of the endovascular wall of the aorta and thus makes the entire blood conduit with stent not easily be moved. On the other hand, the pressure of the blood flowing through the portion of the conduit body in the absence of the expandable stent structure or the threads or the portion of the conduit body disposed with expandable stent structure or the threads which having less expansion strength makes the outer surface of conduit body expand to tightly adhere to the endovascular wall of the aorta.

In the mentioned embodiments, although a corresponding location inside a human's aorta to an end of the portion with the stent structure or the threads possessing larger expansion strength may still form a new tear after the blood conduit with stent is implanted into the human's aorta, the predetermined distance between the stent structure or the threads possessing larger expansion strength and a distal end of the blood conduit with stent prevents the blood passing the distal end of the blood conduit with stent from easily flowing back to the new tear in the corresponding location inside the aorta to the end of the portion with the stent structure or the threads possessing larger expansion strength. This eliminates a possibility that the blood flows back to the false lumen. In other words, an implantation of another stent graft to solve the problems caused by the new tear is no longer required even though the new tear is formed after the disclosed blood conduit with stent is implanted into the aorta. Compared with the well-known arts, the disclosed blood conduit with stent effectively solves the long-term issue of requiring an implantation of another stent graft to treat the new tear and frees patients from the true lumen compression problem caused by the false lumen and the false lumen rupture risk and thus has very great industrial application values. Moreover, the distal end of the disclosed blood conduit with stent is not disposed with a stent structure or a thread possessing larger expansion strength and would not apply excessive radial thrust on the wall of the aorta to which the blood conduit with stent tightly adheres, and therefore a corresponding location of the aorta to the distal end of the blood conduit with stent would not have a new tear.

Description of the embodiments and the accompanying figures will be given below in detail to make the above-mentioned characteristics and advantages of the present invention clearer and easily understood.

Figure 1:
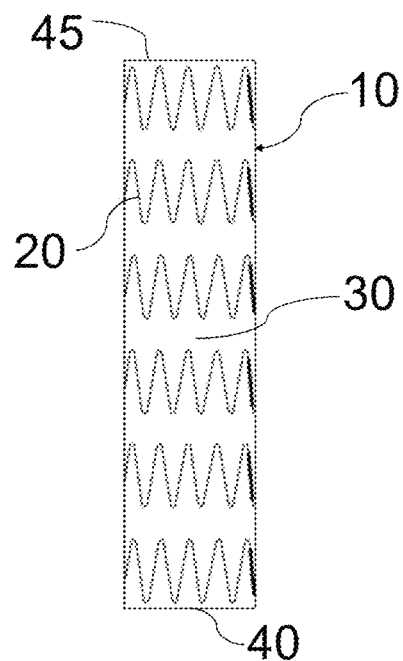
FIG. 1 is a perspective view schematically showing the structure of a typical endovascular stent-graft implanted into an aorta.
Figure 2:
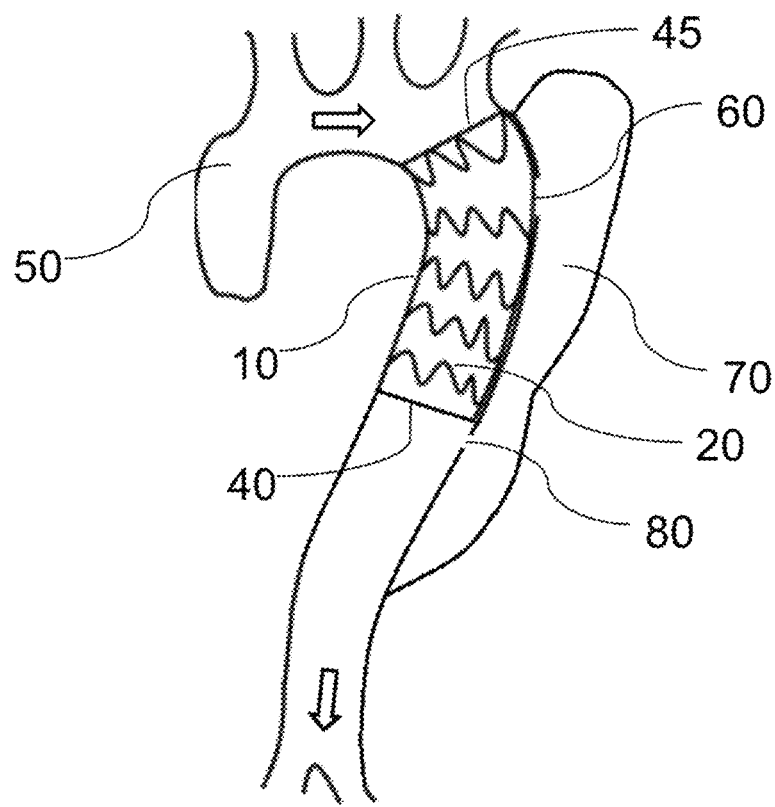
FIG. 2 is a view schematically showing a state in which the typical endovascular stent-graft of FIG. 1 has been implanted into the aorta.

Wherein the description of the numerals in the accompanying figures is as follow.

10 endovascular stent-graft
20 metallic stent
30 artificial blood vessel
40 distal end
45 proximal end
50 aorta
60 tear
70 false lumen 80 new tear
100 folds
200 ventricular assist device
300 pressure gage
400 arrow
600 liquid carrying pipeline
700 titanium alloy vascular ring connector
800 artificial blood vessel
801 proximal end
802 distal end
900 swine thoracic aorta
901 hole
1, 1', 1" blood conduit with stent
11, 11' conduit body
11a, 11a' outer surface
111 first opening end
111a boundary
112 second opening end
112a boundary
12 stent structure
121, 121' threads
121a' boundary
1211 first thread
1211a boundary
1211b ridge peak of waveform
1212 second thread
1212a boundary
1212b ridge peak of waveform
13 another stent structure
1311 third thread
1312 fourth thread
A first portion
B second portion
D outer diameter
D1 calibre
D2 calibre
L axial central line
S distance

DETAILED DESCRIPTION OF THE INVENTION

The present invention discloses a blood conduit with stent and the principles for manufacturing the stent should be well-understood by those skilled in the art and will not be illustrated in detail. Meanwhile, the drawings accompanying the following description are used to schematically illustrate the technical features of the disclosure and are not required to be plotted in a real scale. Furthermore, the phrase "a plurality of" means "be more than two or be equal to two in amount."

Figure 3A:
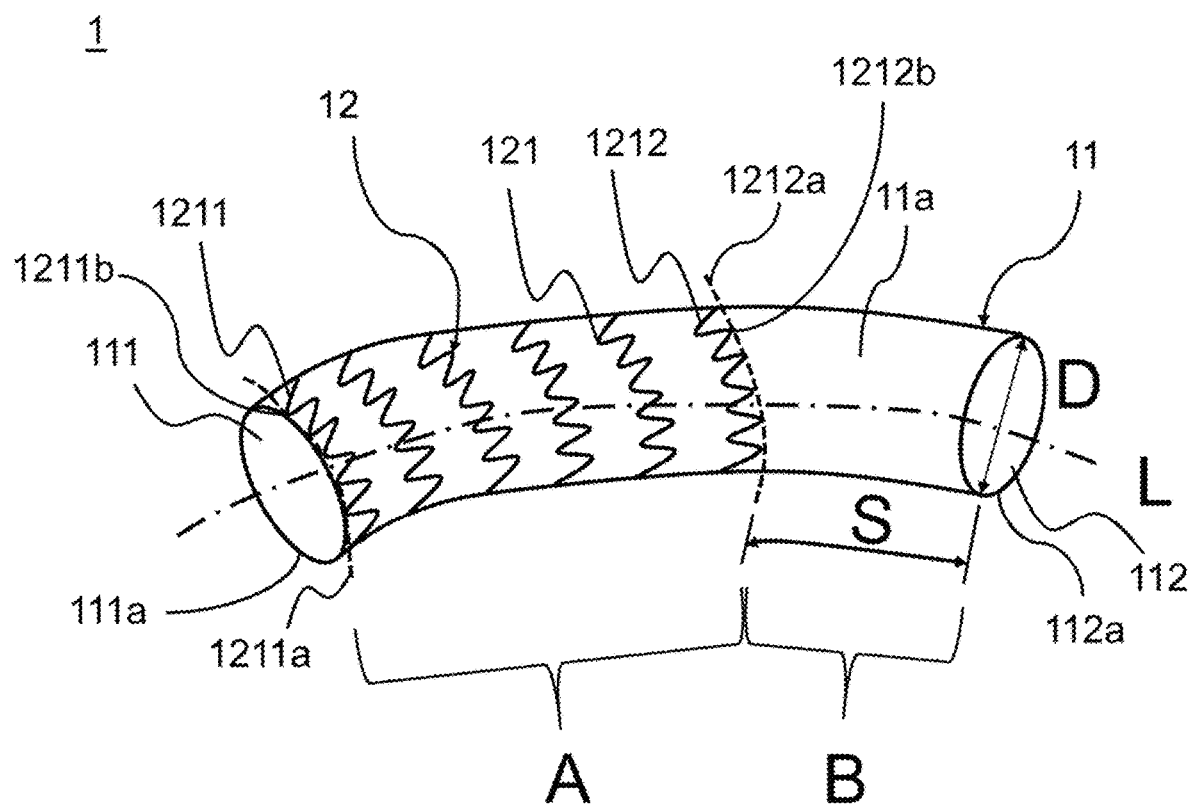
FIG. 3A is a perspective view schematically showing the structure of a blood conduit with stent according to one embodiment of the present disclosure.

FIG. 3A is a perspective view schematically showing the structure of a blood conduit with stent according to one embodiment of the present disclosure. Referring to FIG. 3A, in one embodiment, a blood conduit with stent 1 includes a conduit body 11 and a stent structure 12 mainly composed of a plurality of threads 121. The threads 121 and the whole stent structure 12 are expandable and will be described in detail later. The conduit body 11 has a first opening end 111 through which only an inflow of a blood flowing through the conduit body 11 enters and a second opening end 112 through which only an outflow of the blood flowing through the conduit body 11 leaves. In other words, the blood coming from a human's heart flows into the facing first opening end 111 and out of the second opening end 112 when the blood conduit with stent 1 is implanted into the human's aorta. Therefore, any person skilled in the art could consider that the first opening end 111 serves as a proximal end while the second opening end 112 serves as a distal end of the blood conduit with base stent 1. Moreover, the conduit body 11 must have flexibility of a certain degree with which the structure of the entire conduit body 11 would not be damaged when bended such that the implanted blood conduit with stent 1 can fit various curved paths inside the human's aorta. The flexibility herein means the conduit body 11 could be bended within a certain degree of curvature without damaging its structure. In other words, the conduit body 11 has capability of fitting any curved path inside the human's aorta. In this embodiment, an outer surface 11a of the conduit body 11 is relatively smooth and not folded.

Figure 4:
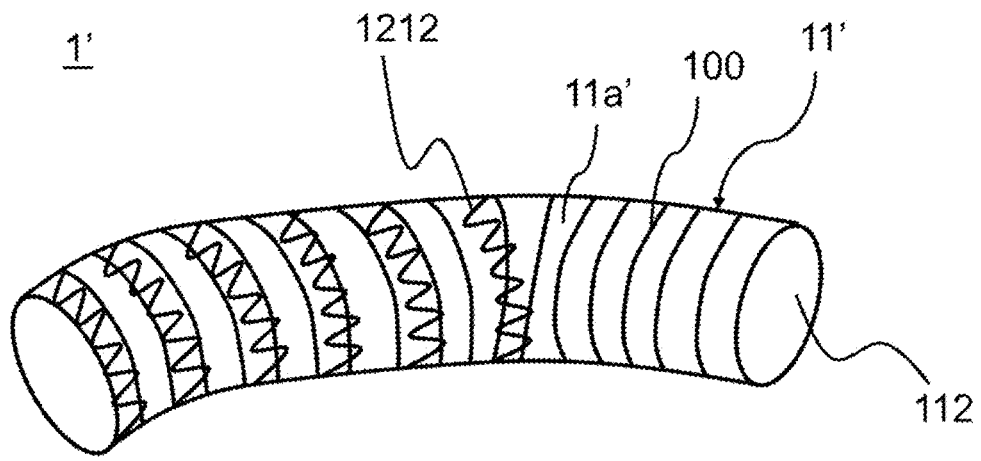
FIG. 4 is a perspective view schematically showing the structure of a blood conduit with stent according to another one embodiment of the present disclosure.

FIG. 4 is a perspective view schematically showing the structure of a blood conduit with stent according to another one embodiment of the present disclosure. Referring to FIG. 4, in another one embodiment, an outer surface 11a' of the conduit body 11' of a blood conduit with stent 1' is formed with folds 100 and the folds render the conduit body 11' as bendable as required to fit various curved path inside the human's aorta.

Referring again to FIG. 3A, on the other hand, each of the threads 121 of the stent structure 12 may have a specific shape such as a periodic fluctuated waveform being but not limited to a wave-shaped, sinusoidal, rectangular, triangular, or jagged waveform or as a non-periodic fluctuated waveform, and may be adhered to the conduit body 11 with a certain arrangement and/or in an interleaving manner. The threads 121 may be adhered to an inner surface or an outer surface 11a of the conduit body 11. The threads 121 may be adhered to the conduit body 11 via sewing or adhesion. In this embodiment, each of the threads 121 is shaped to have a triangular waveform and extend along the circumference of the conduit body 11. The threads 121 are disposed to extend in a direction perpendicular to the axial direction of the conduit body 11 without being interleaved with each other and adhered to the outer surface 11a of the conduit body 11 via adhesion.

Figure 5:
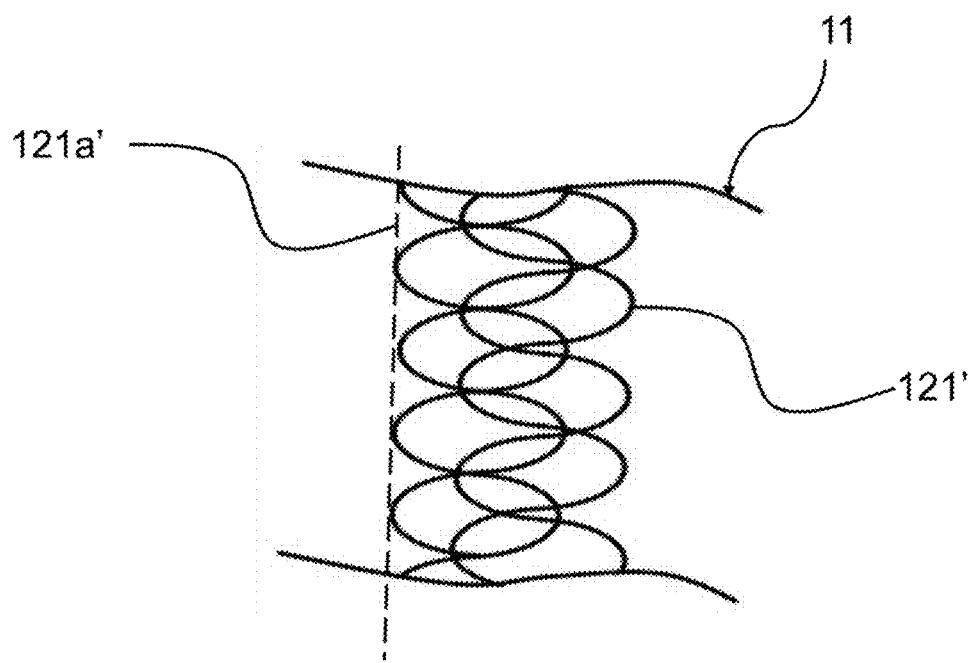
FIG. 5 is a view schematically showing a shape of the threads of the stent structure of a blood conduit with stent according to still another one embodiment of the present disclosure.

FIG. 5 is a view schematically showing a shape of the threads of the stent structure of a blood conduit with stent according to still another one embodiment of the present disclosure. Referring to FIG. 5, in this embodiment, each of the threads 121' is shaped to have an edge-rounded waveform and extend along the circumstance of the conduit body 11. The threads 121' are disposed to extend in a direction perpendicular to the axial direction of the conduit body 11 and interleaved with each other. The above description of the threads 121, 121' and the stent structure 12 is merely used to exemplify the present invention. The shaping and interleaving manner of the threads 121, 121' and the arrangement, adhering manner, and the position of the threads 121, 121' on the conduit body 11 are not limited herein.

Referring again to FIG. 3A, in one embodiment, a boundary 1211a which is a boundary of a first thread 1211 disposed closest to the first opening end 111 and neighbors the first opening end 111 is level with or next to a boundary 111a of the first opening end 111 wherein the first thread 1211 is one of the threads 121 that is disposed closest to the first opening end 111. Moreover, a boundary 1212a which is a boundary of a second thread 1212 disposed closest to the second opening end 112 and neighbors the second opening end 112 is away from a boundary 112a of the second opening end 112 with a distance S wherein the second thread 1212 is one of the threads 121 that is disposed closest to the second opening end 112. The distance S is at least 2 cm. The distance S may range from 2 cm to 30 cm, 2 cm to 13 cm, 2 cm to 10 cm, or 3 cm to 13 cm and preferably from 3 cm to 10 cm.

In one embodiment, the distance S may be varied not along with the change of the outer diameter D of the conduit body 11 but should be greater than or equal to 1 cm (centimeters) regardless of the change of the outer diameter D of the conduit body 11. The distance S may range from 2 cm to 30 cm, 2 cm to 13 cm, 2 cm to 10 cm, or 3 cm to 13 cm. Preferably, the distance S may be 3 cm to 10 cm. In other embodiments, the distance S may be varied along with the change of the outer diameter D of the conduit body 11 and a ratio of the distance S to the outer diameter D of the conduit body 11 should be at least 0.5:1. Generally, the outer diameter D of the conduit body 11 may range from 6 mm (millimeters) to 45 mm and the wall thickness of the conduit body 11 may range from 0.5 mm to 1 mm. Preferably, the distance S may range from 1 cm to 10 cm when the outer diameter D of the conduit body 11 is 6 mm and the distance S may range from 2 cm to 30 cm when the outer diameter D of the conduit body 11 is 16 mm. A ratio of the distance S to the outer diameter D of the conduit body 11 may be 1.25 or greater; a ratio of the distance S to the outer diameter D of the conduit body 11 may range from 1.25 to 50 or from 1.25 to 8.125 and preferably from 1.25 to 6.25.

Figure 6A:
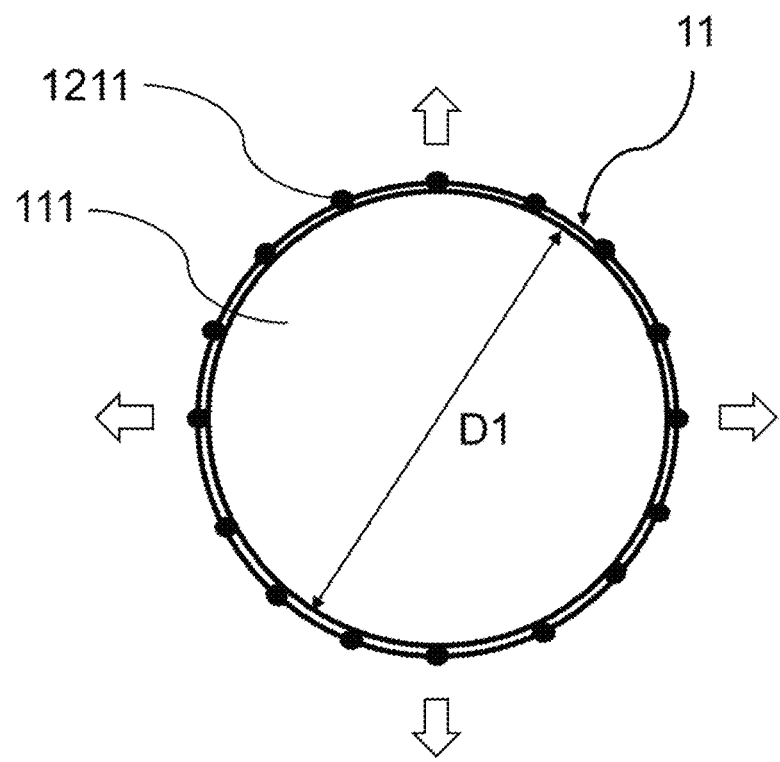
FIG. 6A is a cross-sectional view schematically showing a first opening end of the blood conduit with stent according to one embodiment of the present disclosure.
Figure 6B:
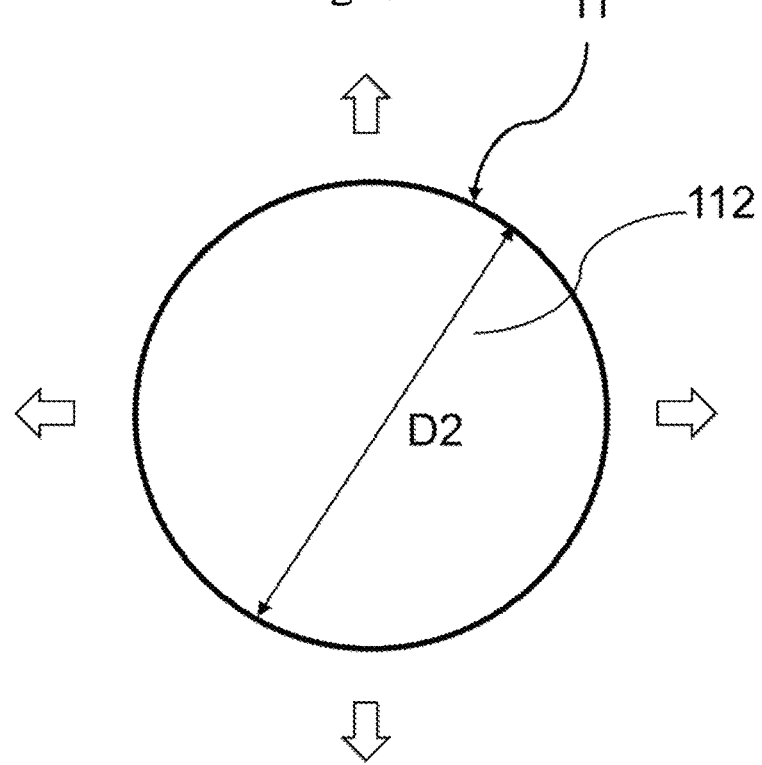
FIG. 6B is a cross-sectional view schematically showing a second opening end of the blood conduit with stent according to one embodiment of the present disclosure.

FIG. 6A is a cross-sectional view schematically showing a first opening end of the blood conduit with stent according to one embodiment of the present disclosure. FIG. 6B is a cross-sectional view schematically showing a second opening end of the blood conduit with stent according to one embodiment of the present disclosure. Referring simultaneously to FIGS. 3A, 6A and 6B, in one embodiment, the first thread 1211 is adhered to the conduit body 11 and adjoins the first opening end 111. Each of the threads 121 and the entire stent structure 12 has expandability, i.e. a space enclosed by boundaries of each of the threads 121 spontaneously becomes greater in the absence of additional forces when each of the threads 121 and the entire stent structure 12 is compressed in a circumstance such as when the whole blood conduit with stent 1 is placed into a blood vessel with an inner diameter being smaller than the outer diameter of the conduit body 11 to compress the conduit body 11, each of the threads 121, and the entire stent structure 12. Besides, the stent structure 12 expands in radial directions intersecting with (i.e. not in parallel with), such as perpendicular to, an axial central line L of the conduit body 11, as shown by the arrows in FIG. 6A. A first portion "A" of the conduit body 11 to which the stent structure 12 is adhered also has expandability such that the structure of the conduit body 11 would not be damaged during the expansion of the stent structure 12. The surround of the second opening end 112 is not adjoined by one of the threads 121 and a second portion "B" of the conduit body 11 from which the stent structure 12 is absent has capability of expanding in radial directions as shown by the arrows in FIG. 6B due to the radial thrust provided by the fluid or blood flowing through the compressed conduit body 11. In one embodiment, the caliber D2 of the second opening end 112 equals the caliber D1 of the first opening end 111. In other embodiments, the caliber D2 of the second opening end 112 may be smaller than the caliber D1 of the first opening end 111 such that the second opening end 112 could be better adhered to the inner wall of the blood vessel during the expansion.

Figure 3B:
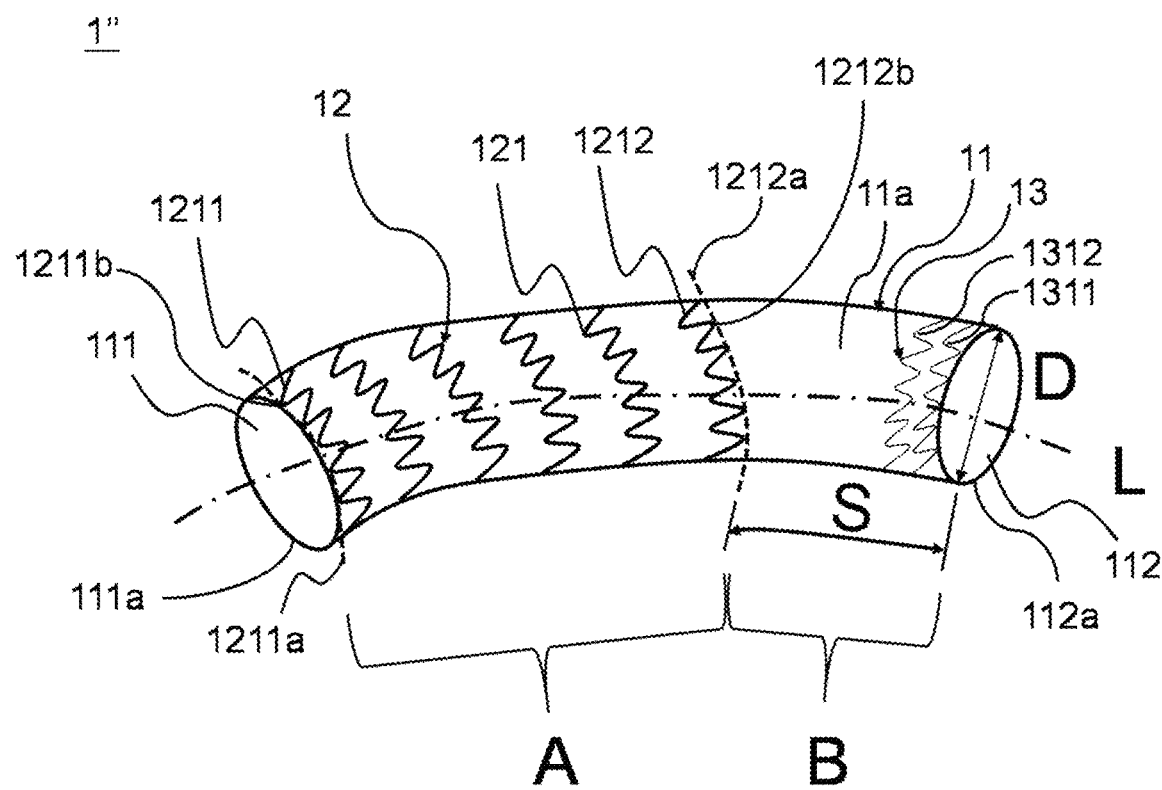
FIG. 3B is a perspective view schematically showing the structure of a blood conduit with stent according to still one embodiment of the present disclosure.

FIG. 3B is a perspective view schematically showing the structure of a blood conduit with stent according to still one embodiment of the present disclosure. Referring to FIG. 3B, in this embodiment, most of the involved elements and their characters are the same as those in FIG. 3A except that the blood conduit with stent 1 further includes at least one additional thread being un-expandable or having expandability with an expansion strength being less than that of each of the threads 121 or the stent structure 12, such as a third thread 1311 and a fourth thread 1312 or another stent structure 13 consisting of these threads that are un-expandable or have less expansion strength than that of the threads 121 or the stent structure 12. The herein mentioned expansion strength means the pressure/force applied to an endovascular wall due to the expansion of the threads or the stent structure and may relate to the deformability and the compressibility of the threads or the stent structure. The third thread 1311 and the third thread 1312 each may have a specific shape such as a periodic fluctuated waveform being but not limited to a wave-shaped, sinusoidal, rectangular, triangular, or jagged waveform or as a non-periodic fluctuated waveform, and may be adhered to the conduit body 11 with a certain arrangement and/or in an interleaving manner. The third thread 1311 and the fourth thread 1312 may be adhered to an inner surface or an outer surface 11a of the conduit body 11. The third thread 1311 and the fourth thread 1312 each may be adhered to the conduit body 11 via sewing or adhesion. In this embodiment, each of the third thread 1311 and the fourth thread 1312 is shaped to have a triangular waveform and extend along the circumference of the conduit body 11. The third thread 1311 and the fourth thread 1312 are disposed to extend in directions perpendicular to the axial direction of the conduit body 11 without being interleaved with each other and adhered to the outer surface 11a of the conduit body 11 via adhesion. The above description of the third thread 1311 and the fourth thread 1312 and the stent structure 13 is merely used to exemplify the present invention. The shaping and interleaving manner of the third thread 1311 and the fourth thread 1312 and the arrangement, adhering manner, and the position of the third thread 1311 and the fourth thread 1312 on the conduit body 11 are not limited herein.

Referring again to FIG. 3B, in this embodiment, the first thread 1211 is disposed closest to a boundary 111a of the first opening end 111, the second thread 1212 is disposed closest to a boundary 112a of the second opening end 112, and a boundary 1212a of the second thread 1212 which neighbors the second opening end 112 is away from the boundary 112a of the second opening end 112 with a distance S. The third thread 1311 and the fourth thread 1312 are disposed within the distance S. The distance S is greater than or equal to 2 cm. The distance S may range from 2 cm to 30 cm, 2 cm to 13 cm, 2 cm to 10 cm, or 3 cm to 13 cm, and preferably from 3 cm to 10 cm.

Referring continuously to FIG. 3B, in this embodiment, when the third thread 1311 and the fourth thread 1312 are un-expandable, they are different from the expandable threads 121 and therefore could not be considered as parts of the expandable stent structure 12. In other words, the compressed second portion "B" of the conduit body 11 to which the stent structure 13 is adhered expands in radial directions as shown by the arrows in FIG. 6B totally due to a radial thrust provided by the fluid or blood flowing through the conduit body 11, though the un-expandable third thread 1311 and the fourth thread 1312 are additionally disposed next to the second opening end 112.

Referring continuously to FIG. 3B, in this embodiment, the third thread 1311 and the fourth thread 1312 may expand in directions perpendicular to the axial direction of the conduit body 11 when the third thread 1311 and the fourth thread 1312 have expandability with a less expansion strength than that of the second thread 1212 or the stent structure 12. In this embodiment, the expansion strength of the third thread 1311 and the fourth thread 1312 is less than or equal to half of the expansion strength of the second thread 1212. Although the expandable third thread 1311 and the fourth thread 1312 are adhered next to the second opening end 112, the compressed second portion "B" of the conduit body 11 to which the stent structure 13 is adhered may still need the radial thrust provided by the fluid or blood flowing through the conduit body 11 to successfully expand in radial directions as shown by the arrows in FIG. 6B for that the expansion strength of the third thread 1311 and the fourth thread 1312 is rather small.

Figure 7A:
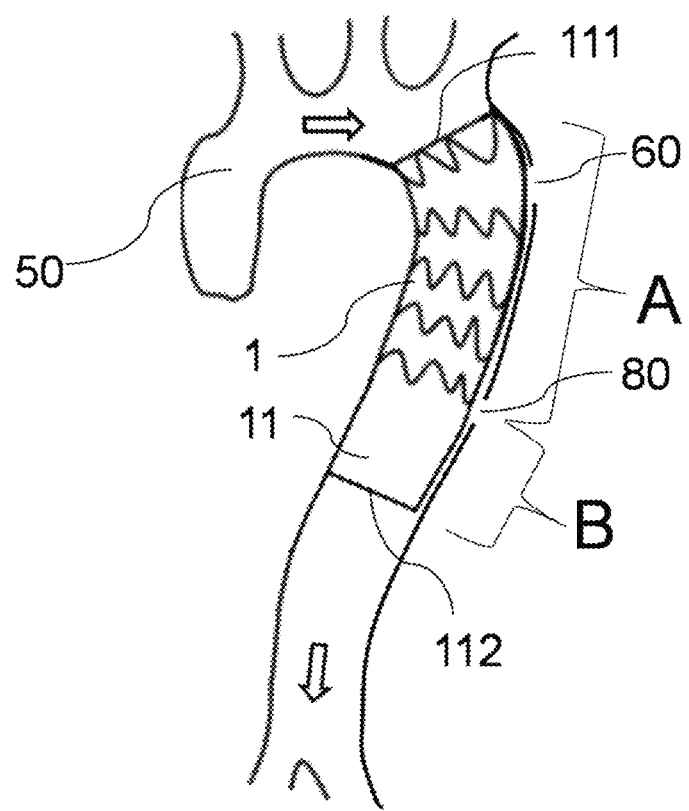
FIG. 7A is a view schematically showing a state in which the blood conduit with stent according to one embodiment of the present disclosure has been implanted into the aortic blood vessel.

FIG. 7A is a view schematically showing a state in which the blood conduit with stent according to one embodiment of the present disclosure has been implanted into the aortic blood vessel. Referring simultaneously to FIGS. 3A and 7A, in one embodiment, when the blood conduit with stent 1 is implanted into a human body's aorta 50, the blood coming from the human body's heart in a direction such as shown by the arrow in the above of FIG. 7A enters the facing first opening end 111 and is guided to leave the second opening end 112 in a direction such as shown by the arrow in the bottom of FIG. 7A. The implantation also makes the first portion "A" of the conduit body 11 between the first opening end 111 and the second thread 1212 isolate the human body's aortic true lumen from a tear 60 in the lesion location. As a result, the radial thrust generated by the outward expansion of the stent structure 12 applies on the aorta 50 and the stent structure 12 tightly adheres to the endovascular wall of the aorta 50 and covers the tear 60 in the lesion location. Furthermore, the expanded stent structure 12 presses against the endovascular wall of the aorta 50 due to the larger size of the expanded stent structure 12 than the inner diameter of the endovascular wall of the aorta 50 and thus makes the entire blood conduit with stent 1 not easily be moved. On the other hand, the second portion "B" of the conduit body 11 between the second thread 1212 and the second opening end 112 is in absence of the stents and the blood pressure of the blood flowing through the second portion "B" make the outer surface of the second portion "B" expand to tightly adhere to the endovascular wall of the aorta 50. Although a corresponding location to an end of the first portion "A" in the aorta 50 may still form a new tear 80 after the blood conduit with stent 1 is implanted into a human body for 1 to 3 years, the second portion "B" prevents the blood passing the second opening end 112 of the blood conduit with stent 1 from easily flowing back to the aortic new tear 80 in the corresponding location to the end of the first portion "A". This eliminates a possibility that the blood flows back to the false lumen. In other words, an implantation of another stent graft to solve the problems caused by the new tear 80 is no longer required even though the new tear 80 is formed after implanting the disclosed blood conduit with stent 1 into the aorta 50. Compared with the well-known arts, the disclosed blood conduit with stent 1 effectively solves the long-term issue of requiring an implantation of another stent graft to treat the new tear 80 and frees patients from the true lumen compression problem caused by the false lumen and the false lumen rupture risk caused by the newly implanted stent graft. Moreover, the surround of the second opening end 112 of the disclosed blood conduit with stent 1 is totally not disposed with a thread or a stent structure and would not apply excessive radial thrust on the endovascular wall of the aorta 50 to which the blood conduit with stent 1 tightly adheres, and therefore a corresponding location of the aorta 50 to the second opening end 112 of the blood conduit with stent 1 would not have a new tear.

Referring back to FIG. 3A, in one embodiment, when each of the threads 121 is shaped to have a triangular waveform, the boundary 1211a of the first thread 1211 which neighbors the first opening end 111 is a line connecting ridge peaks 1211b of the waveform of the first thread 1211 neighboring the first opening end 111, and the boundary 1212a of the second thread 1212 which neighbors the second opening end 112 is a line connecting ridge peaks 1212b of the waveform of the second thread 1212 neighboring the second opening end 112. As shown in FIG. 5, in one embodiment, when each of the threads 121' is shaped to have a periodic edge-rounded waveform, the boundary 121a' of each of the threads 121' is a line connecting ridge peaks of the waveform of each of the threads 121'.

On the other hand, as shown in FIG. 4, an outer surface of a portion of the conduit body 11' between the second thread 1212 and the second opening end 112 is formed with folds when the outer surface 11a' of the flexible conduit body 11' is formed with folds 100. Moreover, in other embodiments, an outer surface of the first portion "A" of the flexible conduit body 11 to which the stent structure 12 is adhered is not folded while an outer surface of the second portion "B" of the flexible conduit body 11 in absence of the stent structure 12 is formed with folds.

Referring again to FIG. 3A, in one embodiment, the first portion "A" of the conduit body 11 between the first opening end 111 and the second thread 1212 and the second portion "B" of the conduit body 11 between the second thread 1212 and the second opening end 112 may be formed in one-piece or connected by two pieces. The first portion "A" and the second portion "B" may be made of the same biocompatible materials. Alternatively, in another one embodiment, the second portion "B" may be made of a distinct material from that of the first portion "A" such that the second portion "B" has better bending adaptability and biocompatibility than that of the first portion "A" in a human body's aortic blood vessel. When the first portion "A" and the second portion "B" of the conduit body 11 are made of the same materials, those materials may be polytetrafluoroethylene (PTFE), polyethylene terephthalate (PET), or Dacron. When the first portion "A" and the second portion "B" of the conduit body 11 are made of distinct materials, a material for the first portion "A" or the second portion "B" may be polytetrafluoroethylene (PTFE), polyethylene terephthalate (PET), or Dacron. A material for the conduit body 11 is not limited herein. On the other hand, a material of the threads 121 may be at least one or a combination of nickel-titanium alloys, shape memory alloys excluding the nickel-titanium alloys, and other biomedical metals.

Figure 7B:
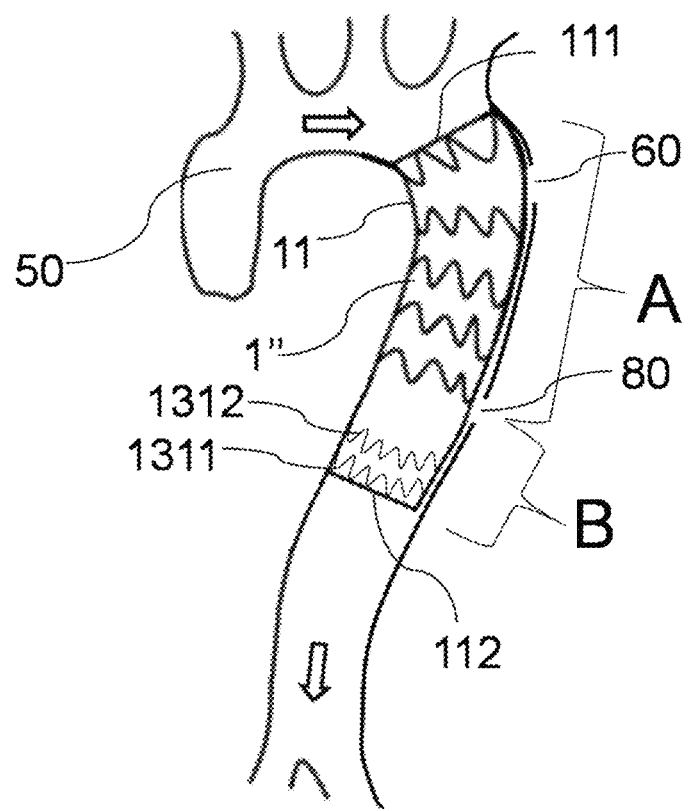
FIG. 7B is a view schematically showing a state in which the blood conduit with stent according to still one embodiment of the present disclosure has been implanted into the aortic blood vessel.

FIG. 7B is a view schematically showing a state in which the blood conduit with stent according to still one embodiment of the present disclosure has been implanted into the aortic blood vessel.

Referring simultaneously to FIGS. 3B and 7B, in still one embodiment, when the stent structure 13, the third thread 1311, and the fourth thread 1312 are un-expandable, an outer surface of the compressed second portion "B" of the conduit body 11, to which the stent structure 13, the third thread 1311, and the fourth thread 1312 are adhered, expands due to blood pressure provided by the fluid or blood flowing through the second portion "B" and therefore adheres to the endovascular wall of the human's aorta 50, though the un-expandable stent structure 13, the third thread 1311, and the fourth thread 1312 are additionally disposed within the second portion "B" between the expandable second thread 1212 and the second opening end 112. The second portion "B" prevents the blood passing the second opening end 112 of the blood conduit with stent 1" from easily flowing back to the new tear 80 in a corresponding location of the aorta 50 to the end of the first portion "A" and therefore eliminates a possibility that the blood flows back to the false lumen. In other words, an implantation of another stent graft to solve the problems caused by the new tear 80 is no longer required even though the new tear 80 is formed after implanting the disclosed blood conduit with stent 1" into the aorta 50. Compared with the well-known arts, the disclosed blood conduit with stent 1" effectively solves the long-term issue of requiring an implantation of another stent graft to treat the new tear 80 and frees patients from the true lumen compression problem caused by the false lumen and the false lumen rupture risk caused by the newly implanted stent graft. Moreover, the surround of the second opening end 112 of the disclosed blood conduit with stent 1" would not apply excessive radial thrust on the endovascular wall of the aorta 50 to which the blood conduit with stent 1" tightly adheres, and therefore a corresponding location of the aorta 50 to the second opening end 112 of the blood conduit with stent 1" would not have a new tear because the stent structure 13, the third thread 1311, and the fourth thread 1312 disposed next to the second opening end 112 are un-expandable.

Referring simultaneously to FIGS. 3B and 7B, in still one embodiment, when the stent structure 13, the thread 1311, and the fourth thread 1312 are expandable but has less expandability strength than that of the second thread 1212, an outer surface of the compressed second portion "B" of the conduit body 11 expands due to both the weaker expansion strength of the stent structure 13, the thread 1311, and the fourth thread 1312 or/and the pressure of the blood flowing through the second portion "B" and then adheres to the endovascular wall of the human's aorta 50, though the stent structure 13, the third thread 1311, and the fourth thread 1312 are additionally disposed within the second portion "B" between the second thread 1212 possessing greater expansion strength and the second opening end 112. The second portion "B" prevents the blood passing the second opening end 112 of the blood conduit with stent 1" from easily flowing back to the new tear 80 of the aorta 50 in a corresponding location to the end of the first portion "A" and therefore eliminates a possibility that the blood flows back to the false lumen. In other words, an implantation of another stent graft to solve the problems caused by the new tear 80 is no longer required even though the new tear 80 is formed after implanting the disclosed blood conduit with stent 1" into the aorta 50. Compared with the well-known arts, the disclosed blood conduit with stent 1" effectively solves the long-term issue of requiring an implantation of another stent graft to solve the new tear 80 and frees patients from the true lumen compression problem caused by the false lumen and the false lumen rupture risk caused by the newly implanted stent graft. Moreover, the second opening end 112 of the disclosed blood conduit with stent 1" would not apply excessive radial thrust on the endovascular wall of the aorta 50 to which the blood conduit with stent 1" tightly adheres, and therefore a corresponding location of the aorta 50 to the second opening end 112 of the blood conduit with stent 1" would not have a new tear because the expansion strength of the stent structure 13, the third thread 1311, or the fourth thread 1312 disposed next to the second opening end 112 is rather small.

Figure 8:
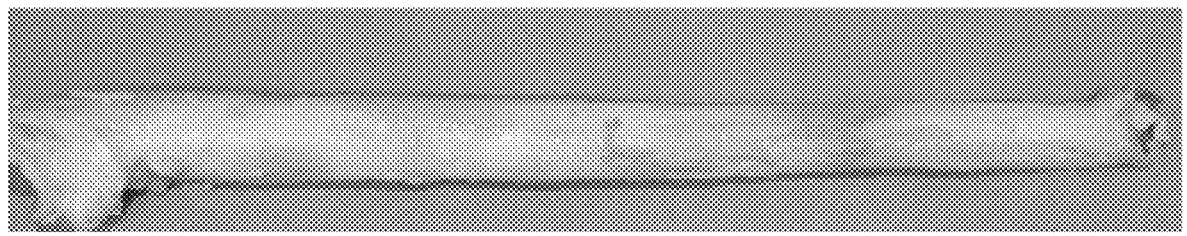
FIG. 8 is a picture of a swine thoracic aorta.
Figure 9:
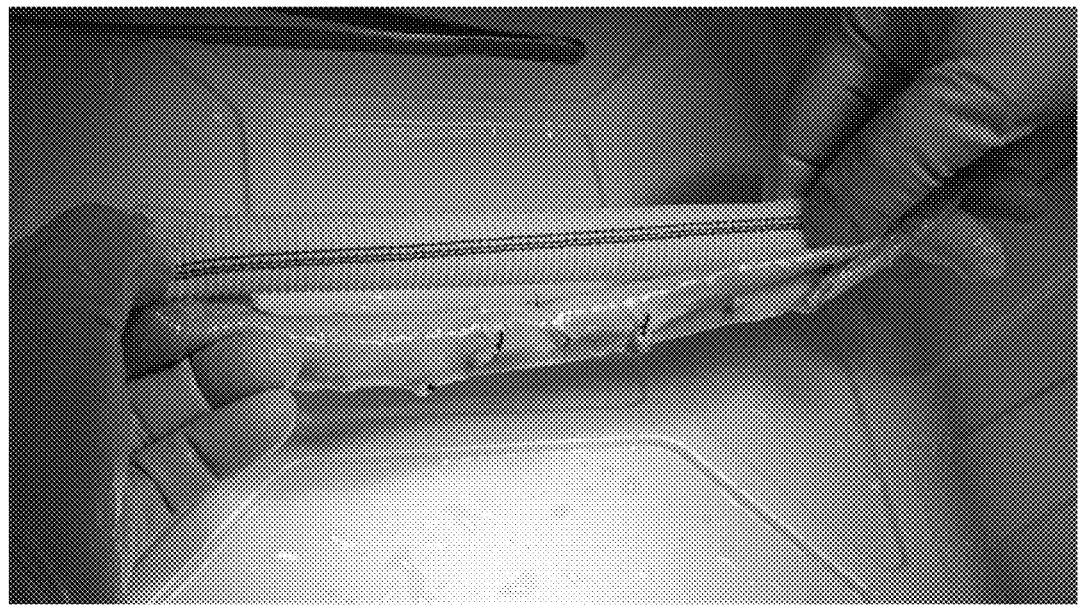
FIG. 9 is a picture of an artificial blood vessel and a swine thoracic aorta in comparison.

Referring to FIGS. 7A, 7B, and 9, the following description explain how the second portion "B" prevents the blood passing the second opening end 112 from flowing back to the new tear 80 of the human aorta 50 in a location corresponding to the end of the first portion "A" and flowing into the false lumens when the new tear 80 is formed around the end of the first portion "A" after the disclosed blood conduit with stent is implanted into the human's aorta 50. The following description further gives preferred values for the length of the second portion "B", i.e. the distance S as shown in the FIGS. 3A and 3B, and preferred values for the ratio of the length of the second portion "B", i.e. the distance S as shown in the FIGS. 3A and 3B, to the outer diameter of the second portion "B", i.e. the outer diameter D of the conduit body 11 as shown in FIGS. 3A and 3B. The inventor used a commercially available adult swine thoracic aorta to simulate the aorta 50 in FIG. 7A and FIG. 7B, and then punched holes on said adult swine thoracic aorta to simulate the new tear 80 formed around the end of the first portion "A" in FIG. 7A and FIG. 7B, and fixed the proximal end of an artificial blood vessel upstream of the punched hole while kept the distal end detached (that is, not fixed to the swine aorta) downstream of the punched hole to use said artificial blood vessel to simulate the second portion "B" of the blood conduits with stent 1 or 1" in FIG. 7A and FIG. 7B. FIG. 8 is a picture of a swine thoracic aorta. FIG. 9 is a picture of an artificial blood vessel and a swine thoracic aorta in comparison.

Figure 10:
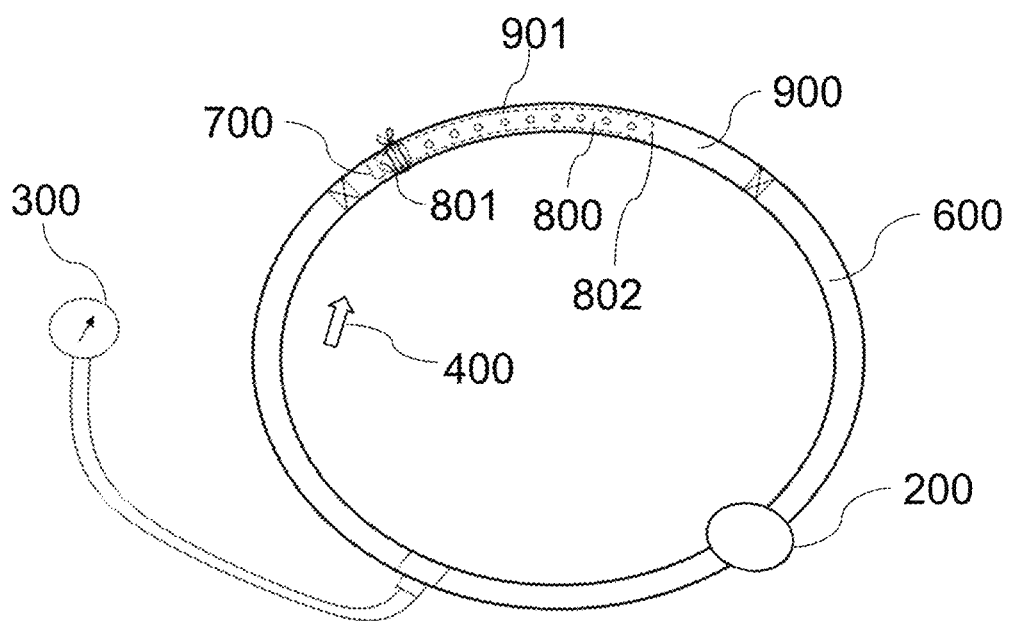
FIG. 10 is view schematically showing a simulated aortic blood flow in a closed recirculating pipe line made by implanting an artificial blood vessel without having a stent structure into the swine thoracic aorta and connecting the swine thoracic aorta with a liquid carrying pipeline, a ventricular assist device, and a pressure gage.

The experimental procedure of the embodiments is described below. Please refer to FIG. 10. FIG. 10 is view schematically showing a simulated aortic blood flow in a closed recirculating pipe line made by implanting an artificial blood vessel without having a stent structure into the swine thoracic aorta and connecting the swine thoracic aorta with a liquid carrying pipeline, a ventricular assist device, and a pressure gage. First, an artificial blood vessel 800 without stent was placed in the lumen of a swine thoracic aorta 900. A proximal end 801 of the artificial blood vessel 800 was fixed to the swine thoracic aorta 900 using a titanium alloy vascular ring connector 700, and a distal end 802 of the artificial blood vessel 800 remained detached (that is, not fixed to the swine thoracic aorta). Next, the swine thoracic aorta 900 was connected a liquid carrying pipeline 600 (such as a Tygon Tube) and a Ventricular Assist Device (VAD) 200, and infused with a simulated blood fluid to construct a simulated aortic blood flow in a closed recirculating pipeline to simulate the flow of the aortic blood flow in the second portion "B" of the conduit body of the blood conduit with stent in the aforementioned embodiments. The direction of flow of the simulated blood fluid was clockwise as shown by an arrow 400 in FIG. 10. The closed recirculating pipeline and the simulated aortic blood flow in it was further connected to a pressure gage 300. Next, holes were punched with certain spacing on the swine thoracic aorta 900 in a region corresponding to the region between the proximal end 801 and the distal end 802 of the artificial blood vessel 800, and the leakage velocity of the simulated blood fluid through each hole 901 was monitored. Wherein, a $10^{th}$ hole was punched at a location on the swine thoracic aorta 900 corresponding to the location between the proximal end 801 and the distal end 802 and away from the distal end 802 of the artificial blood vessel 800 with a distance of 13 cm, and the leakage velocity of the simulated blood fluid through the $10^{th}$ hole was monitored to simulate and observe the situation of blood passing the second opening end 112 and back flowing to a location on the aorta 50 corresponding to the new tear 80 at the end of the first portion "A" and thus flowing into the false lumen under the condition that the length of the second portion "B" of the blood conduits with stent 1 or 1" in FIG. 7A and FIG. 7B (that is, the distance S in FIG. 3A and FIG. 3B) was 13 cm. Once the observation at the $10^{th}$ hole was completed, the tenth hole was sutured, and a $9^{th}$ hole was punched at a location on the swine thoracic aorta 900 corresponding to the location between the proximal end 801 and the distal end 802 and away from the distal end 802 of the artificial blood vessel 800 with a distance of 12 cm, and the leakage velocity of the simulated blood fluid through the $9^{th}$ hole was monitored to simulate and observe the situation of blood passing the second opening end 112 and back flowing to a location of the aorta 50 corresponding to the new tear 80 at the end of the first portion "A" and thus flowing into the false lumen under the condition that the length of the second portion "B" of the blood conduits with stent 1 or 1" in FIG. 7A and FIG. 7B (that is, the distance S in FIG. 3A and FIG. 3B) was 12 cm. Upon completing the observation at the $n^{th}$ hole, the $n^{th}$ hole was sutured, and the next hole was punched at a location on the swine thoracic aorta 900 corresponding to the location between the proximal end 801 and the distal end 801 and closer to the distal end 802 of the artificial blood vessel 800 to perform the same observation, and so on and so forth.

Please refer to FIG. 10. In this experiment, the simulated aortic blood fluid was made of 450 g sugar in 1500 mL of water to achieve a serum viscosity similar to that of a normal human body; that is, 4 cP (centipoise). The proximal end 801 of the artificial blood vessel 800 was the inflow end of the simulated blood fluid. The distal end 802 of the artificial blood vessel 800 was the outflow end of the simulated blood fluid. The outer diameter of the artificial blood vessel 800 was 16 mm, the inner diameter was 15 mm, and the material of the artificial blood vessel was Dacron. The circulating flow velocity of the simulated aortic blood fluid was controlled at 4.2 liters per minute using the Ventricular Assist Device (VAD) 200, the average pressure was 60 mmHg as measured by the pressure gage 300, and the diameter of each hole 901 was about 0.4-0.5 cm.

Based on the results of this experiment, it was found that when the hole is further away from the distal end 802 of the artificial blood vessel 800, the leakage velocity of the simulated blood fluid is slower, as shown in Table 1. Using the $10^{th}$ hole and the $3^{rd}$ hole as examples, the descriptions are as follows.

Figure 11:
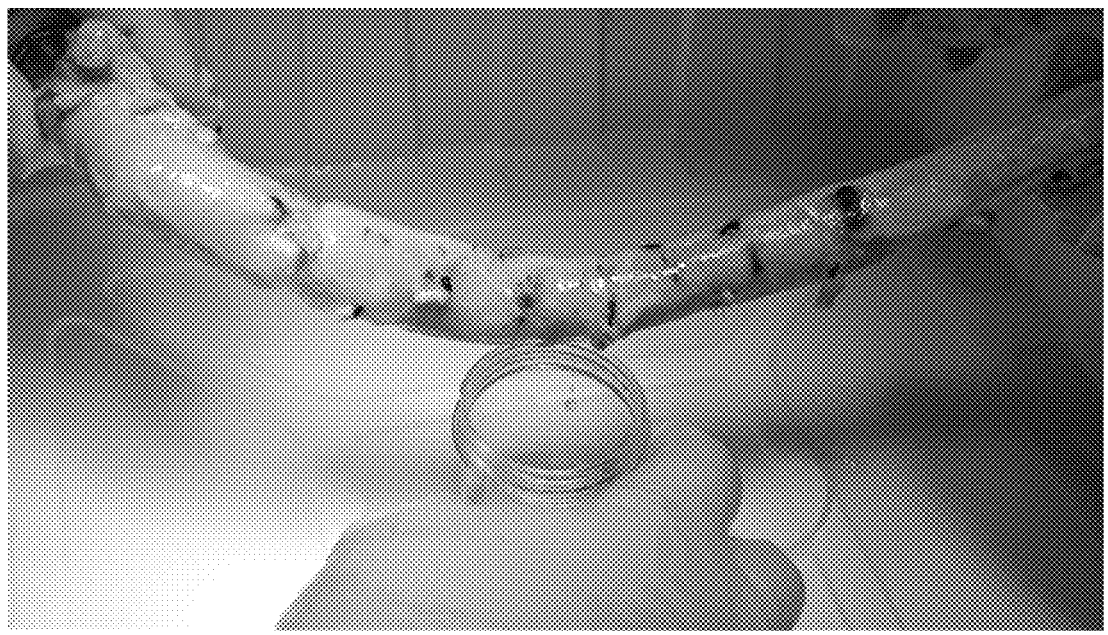
FIG. 11 is a picture showing a leakage through the $10^{th}$ hole of the artificial blood vessel used in FIG. 10.
Figure 12:
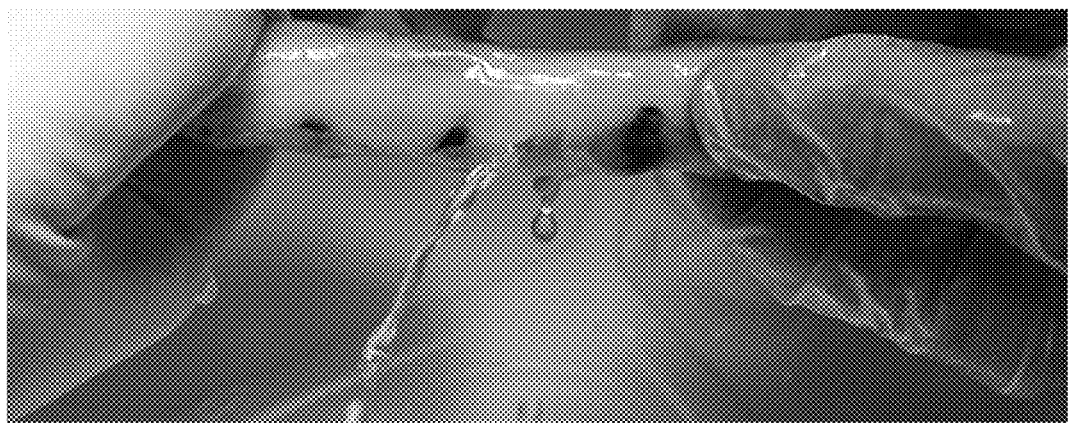
FIG. 12 is a picture showing a leakage through the $3^{rd}$ hole of the artificial blood vessel used in FIG. 10.

Please refer to FIG. 11 and FIG. 12. FIG. 11 is a picture showing a leakage through the $10^{th}$ hole of the artificial blood vessel used in FIG. 10. FIG. 12 is a picture showing a leakage through the $3^{rd}$ hole of the artificial blood vessel used in FIG. 10. FIG. 11 demonstrates that the leakage velocity of the simulated blood fluid out flowing through the $10^{th}$ hole (that is, the hole away from the distal end 802 of the artificial blood vessel 800 with a distance of 13 cm) is very slow. In other words, the volume of the simulated blood fluid out flowing through the $10^{th}$ hole is very small. This demonstrates that it is less likely for the simulated blood fluid passing the distal end 802 of the artificial blood vessel 800 to back flow and leak through the punched aortic hole away from the distal end 802 with a distance of 13 cm. FIG. 12 demonstrates that the leakage velocity of the simulated blood fluid out flowing through the $3^{rd}$ hole (that is, the hole away from the distal end 802 of the artificial blood vessel 800 with a distance of 1.5 cm) is not very slow. In other words, the volume of the simulated blood fluid out flowing through the $3^{rd}$ hole is not very small. This demonstrates that it is still likely for the simulated blood fluid passing the distal end 802 of the artificial blood vessel 800 to back flow and leak through the punched aortic hole away from the distal end 802 with a distance of 1.5 cm.

TABLE 1

| Number of the hole | Distance between the hole and the distal end of the artificial blood vessel (cm) | Circulating flow velocity (liter/minute) | Average pressure (mmHg) | Leakage velocity (mL/minute) | Extent of leakage decreased (%) |
|---|---|---|---|---|---|
| 1 | 0 | 4.2 | 60 | 1,610 | 0 |
| 2 | 1 | 4.2 | 60 | 350 | 78 |
| 3 | 1.5 | 4.2 | 60 | 240 | 85 |
| 4 | 2 | 4.2 | 60 | 45 | 97 |
| 5 | 3 | 4.2 | 60 | 32 | 98 |
| 6 | 5 | 4.2 | 60 | 32 | 98 |
| 7 | 7 | 4.2 | 60 | 33 | 98 |
| 8 | 9 | 4.2 | 60 | 32 | 98 |
| 9 | 11 | 4.2 | 60 | 31 | 98 |
| 10 | 13 | 4.2 | 60 | 30 | 98 |

Figure 13:
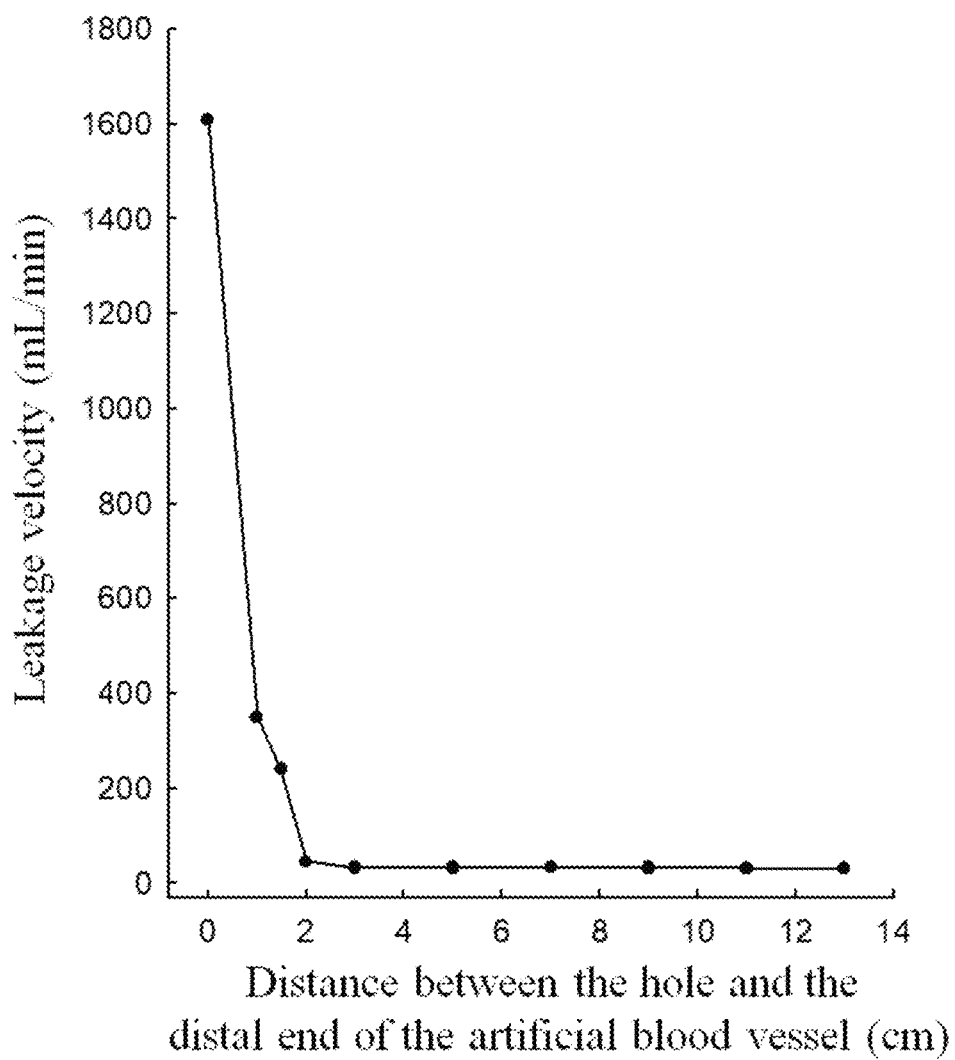
FIG. 13 is a diagram showing an effect of the distance between a hole of the swine thoracic aorta and the distal end of the artificial blood vessel on the leakage velocity of a simulated blood fluid.

Please refer to Table 1 and FIG. 13. The results in Table 1 and FIG. 13 indicate that a large amount of simulated blood fluid back flows to the hole 901 of the swine thoracic aorta 900 when the distance between the hole 901 and the distal end 802 of the artificial blood vessel 800 is 1.5 cm or shorter. When the distance between the hole 901 and the distal end 802 of the artificial blood vessel 800 is equal to 2 cm, the extent of leakage is effectively decreased by 97%, thereby reducing the incidence of backflow. Thus, in terms of the function of preventing the simulated blood fluid from leaking through the new tear of the aorta, that the length of the second portion "B" of the blood conduit with stent in the present invention is greater than or equal to 2 cm is a preferable important characteristic. Additionally, when the distance between the hole 901 and the distal end 802 of the artificial blood vessel 800 is equal to 3 cm, the extent of leakage is effectively decreased by 98%, and the extent of leakage is not further decreased comparing to longer distances. Thus, in terms of the function of preventing simulated blood fluid from leaking through the new tear of the aorta, that the length of the second portion "B" of the blood conduit with stent in the present invention is greater than or equal to 3 cm is a more preferable important characteristic. Preferably, when the inner diameter of the artificial blood vessel 800 is 15 mm, the distance between the distal end 802 of the artificial blood vessel 800 and the hole 901 may be 3 cm to 30 cm. In other words, in regard of the blood conduits with stent 1 or 1" in the embodiments of the present invention, when the inner diameter of the conduit body 11 is 15 mm, the length of the second portion "B" of the conduit body 11 or the distance S between the second opening end 112 (that is, the distal end) and the second thread 1212, which is closest to the second opening end 112, of the expandable stent structure 12 of great expansion strength, may be 3 cm to 30 cm. This can effectively prevent the blood passing the second opening end 112 of the blood conduit with stent 1 (or 1") from back flowing to a location in the conduit body 11 corresponding to the location of the second thread 1212, and further prevent the blood from back flowing into the original false lumen or forming a new false lumen near the second thread 1212. Alternatively, the distance S may be 3 cm to 13 cm. Preferably, the distance S may be 3 cm to 10 cm.

It needs to be described that slower flow velocity of the blood (for example, slower than or equal to 45 mL/minute) flowing out through the tear allows for sufficient time for coagulation reaction to occur due to the smaller volume of blood flowing through the tear, thereby gradually blocking the tear. According to the simulation results of this experiment, when the length of the second portion "B" of the blood conduit with stent in the present invention is greater or equal to 2 cm, there is sufficient time for the blood flowing out from the new tear to coagulate even though the leakage velocity of the flowing blood from the new tear may reach 30-45 mL/minute during new tear formation, thereby gradually blocking the new tear and eventually leading to complete hemostasis.

By converting the aforementioned experimental data, it is found that when the ratio of the distance between the distal end 802 of the artificial blood vessel 800 and the hole to the outer diameter of the artificial blood vessel 800 is larger, the leakage velocity of the simulated blood fluid is slower, as shown in Table 2. Using the $10^{th}$ hole as an example, the calculation method for the ratio of the distance between the distal end of the artificial blood vessel and the hole to the outer diameter of the artificial blood vessel is demonstrated as follows. The distance between the distal end of the artificial blood vessel and the $10^{th}$ hole is 13 cm, and the outer diameter of the artificial blood vessel is 16 mm, so the ratio of the two is 13±1.6=8.125.

TABLE 2

| Number of the holes | Distance between the hole and the distal end of the artificial blood vessel (cm) | Circulating flow velocity (liter/minute) | Average pressure (mmHg) | Leakage velocity (mL/minute) | Extent of leakage decreased (%) |
|---|---|---|---|---|---|
| 1 | 0 | 4.2 | 60 | 1,610 | 0 |
| 2 | 0.625 | 4.2 | 60 | 350 | 78 |
| 3 | 0.9375 | 4.2 | 60 | 240 | 85 |
| 4 | 1.25 | 4.2 | 60 | 45 | 97 |
| 5 | 1.875 | 4.2 | 60 | 32 | 98 |
| 6 | 3.125 | 4.2 | 60 | 32 | 98 |
| 7 | 4.375 | 4.2 | 60 | 33 | 98 |
| 8 | 5.625 | 4.2 | 60 | 32 | 98 |
| 9 | 6.875 | 4.2 | 60 | 31 | 98 |
| 10 | 8.125 | 4.2 | 60 | 30 | 98 |

Please refer to Table 2. Results in Table 2 demonstrate that when the ratio of the distance between the distal end of the artificial blood vessel and the hole to the outer diameter of the artificial blood vessel is smaller than or equal to 0.9375, large amount of the simulated blood fluid back flows to the hole of the swine thoracic aorta. However, when the ratio of the distance between the distal end of the artificial blood vessel and the hole to the outer diameter of the artificial blood vessel is equal to 1.25, the extent of leakage is effectively decreased by 97%, thereby reducing the incidence of backflow. Therefore, in terms of the function of effectively preventing the simulated blood fluid from leaking through the new tear of the aorta, that the ratio of the length of the second portion "B" of the blood conduit with stent in the present invention to the outer diameter of the second portion B is greater than or equal to 1.25 is a preferable important characteristic. When the ratio of the distance between the distal end of the artificial blood vessel and the hole to the outer diameter of the artificial blood vessel is 1.875, the extent of leakage is effectively decreased by 98%, and the leakage is not further decreased when comparing to longer distances. Therefore, in terms of the function of effectively preventing the simulated blood fluid from leaking through the new tear of the aorta, that the ratio of the length of the second portion "B" of the blood conduit with stent in the present invention to the outer diameter of the second portion "B" is greater than or equal to 1.875 is a more preferable important characteristic. In this regard, the ratio of the length of the second portion "B" of the blood conduit with stent in the present invention to the outer diameter of the second portion "B" is at least 1.8. Alternatively, the ratio of the length of the second portion "B" of the blood conduit with stent in the present invention to the outer diameter of the second portion "B" may be 1.8 to 50. Alternatively, the ratio of the length of the second portion "B" of the blood conduit with stent in the present invention to the outer diameter of the second portion B may be 1.8 to 8.125. Preferably, the ratio of the length of the second portion "B" of the blood conduit with stent in the present invention to the outer diameter of the second portion "B" is 1.8 to 6.25.

It needs to be described that slower flow velocity of the blood (for example, slower than or equal to 45 mL/minute) flowing out through the tear allows for sufficient time for coagulation reaction to occur due to the smaller volume of the blood flowing through the tear, thereby gradually blocking the tear. According to the simulation results of this experiment, when the ratio of the length of the second portion "B" of the blood conduit with stent in the present invention to the outer diameter of the second portion "B" is greater than or equal to 1.25, there is sufficient time for the blood flowing out from the new tear to coagulate even though the leakage velocity of the flowing blood from the new tear may reach 30-45 mL/minute during new tear formation, thereby gradually blocking the new tear and eventually leading to complete hemostasis.

According to the simulation results of the aforementioned experiment, the length of the second portion "B" in the present invention (that is, the distance S in FIG. 3A or FIG. 3B) may be 2 cm to 30 cm, 2 cm to 13 cm, and preferably 2 cm to 10 cm. On the other hand, the ratio of the length of the second portion "B" in the present invention (that is, the distance S in FIG. 3A or FIG. 3B) to the outer diameter of the second portion "B" (that is, the outer diameter D of the conduit body 11 in FIG. 3A and FIG. 3B) may be 1.25, 1.25 to 50, 1.25 to 8.125, and preferably 1.25 to 6.25.

In the embodiments as mentioned, the effect of applying radial thrust on the aorta via the outward expansion of the stent structure or the threads with larger expansion strength makes the stent structure or the threads with larger expansion strength tightly adhere to the endovascular wall of a human's aorta and cover a tear in the lesion location. The expanded stent structure presses against the endovascular wall of the aorta due to the larger size of the expanded stent structure than the inner diameter of the endovascular wall of the aorta and thus makes the entire blood conduit with stent not easily be moved. On the other hand, the pressure of the blood flowing through the portion of the conduit body in the absence of the expandable stent structure or the threads or the portion of the conduit body disposed with expandable stent structure or the threads which having less expansion strength makes the outer surface of conduit body expand to tightly adhere to the endovascular wall of the aorta. Although a corresponding location inside a human's aorta to an end of the portion with the stent structure or the threads possessing larger expansion strength may still form a new tear after the blood conduit with stent is implanted into the human's aorta, the predetermined distance between the stent structure or the threads possessing larger expansion strength and a distal end of the blood conduit prevents the blood passing the distal end of the blood conduit with stent from easily flowing back to the new tear in the corresponding location inside the aorta to the end of the portion with the stent structure or the threads possessing larger expansion strength. This eliminates a possibility that the blood flows back to the original false lumen. In other words, an implantation of another stent graft to solve the problems caused by the new tear is no longer required even though the new tear is formed after the disclosed blood conduit with stent is implanted into the aorta. Compared with the well-known arts, the disclosed blood conduit with stent effectively solves the long-term issue of requiring an implantation of another stent graft to treat the new tear and frees patients from the true lumen compression problem caused by the false lumen and the false lumen rupture risk and thus has very great industrial application values. Moreover, the distal end of the disclosed blood conduit with stent would not apply excessive radial thrust on the wall of the aorta to which the blood conduit with stent tightly adheres, and therefore a corresponding location of the aorta to the distal end of the blood conduit with stent would not have a new tear.

The above-mentioned are merely descriptions of preferred embodiments of the present disclosure. Based on the same or similar principles, the blood conduit with stent in the present invention may be broadly applied to the treatments for vascular dissection, including but not limited to arterial dissection, venous dissection, aortic dissection, Stanford type A aortic dissection, Stanford type B aortic dissection, DeBakey Type I aortic dissection, DeBakey Type II aortic dissection, and DeBakey Type III aortic dissection. Preferably, it is used to treat aortic dissection. Preferably, it is used to treat Stanford type B aortic dissection.

Based on the same or similar principles, the blood conduit with stent in the present invention can be used to treat blood vessel dilation, including but not limited to aneurysm, venous aneurysm, aortic aneurysm, thoracic aortic aneurysm, ascending aortic aneurysm, aortic arch aneurysm, descending aortic aneurysm, and abdominal aortic aneurysm. Preferably, it is used to treat descending aortic aneurysm.

The above-mentioned are merely preferred embodiments of the present disclosure, and shall not be used to limit the scope of the appended claims. Further, those skilled in the art will understand from the description set forth, and practice the present disclosure according thereto. Thus, other equivalent alterations and modifications which are completed without departing from the spirit disclosed by the present disclosure should be included in the scope of the appended claims.

What is claimed is:

1. A blood conduit with stent used in an implantation into a thoracic aorta, comprising:
 a flexible conduit body with only two opening ends, having:
  a first opening end through which only an inflow of a blood of the thoracic aorta enters;
  a second opening end through which only an outflow of the blood of the thoracic aorta leaves;
  a first thread adhered to a first portion of the flexible conduit body and disposed to be close to a boundary of the first opening end;
  a second thread adhered to the first portion of the flexible conduit body and disposed to be near a boundary of the second opening end with a boundary of the second thread being spaced from the boundary of the second opening end with a distance ranging from 2 cm to 30 cm;
  a second portion of the flexible conduit body being free of the first thread and the second thread and positioned between the boundary of the second thread and the boundary of the second opening end; and
  a third thread adhered to the second portion of the flexible conduit body and disposed within a region between the boundary of the second thread and the boundary of the second opening end;
 wherein the third thread has an expansion strength less than an expansion strength of the second thread, and the second portion of the flexible conduit body has function of being adhered to an endovascular wall of the thoracic aorta due to the radial thrust provided by the blood flowing through the flexible conduit body to prevent the blood leaving the second opening end from back flowing into a location of the thoracic aorta near the second thread when the implantation is completed.

2. The blood conduit with stent of claim 1, wherein the expansion strength of the third thread is less than or equal to half of the expansion strength of the second thread.

3. The blood conduit with stent of claim 1, wherein the third thread is adhered to an inner surface of the second portion of the flexible conduit body, and the first thread and the second thread are adhered to an outer surface of the first portion of the flexible conduit body.

4. The blood conduit with stent of claim 1, wherein a material of the first, second or third thread is at least one or a combination of nickel-titanium alloys, shape memory alloys excluding the nickel-titanium alloys, and other biomedical metals.

5. The blood conduit with stent of claim 1, wherein each of the first, second and third thread is shaped to have a periodic fluctuated waveform and extend in a direction perpendicular to an axial direction of the flexible conduit body, and the boundary of the second thread is a line connecting ridge peaks of the periodic fluctuated waveform of the second thread with the ridge peaks neighboring the second opening end.

6. The blood conduit with stent of claim 1, wherein the first portion of the flexible conduit body is made of a different material from that of the second portion of the flexible conduit body.

7. A method of treating an aortic disease, comprising: implanting the blood conduit with stent of claim 1 into a thoracic aorta.

* * * * *